(12) United States Patent
Eisenkolb

(10) Patent No.: US 7,485,129 B2
(45) Date of Patent: Feb. 3, 2009

(54) DEVICE FOR COMPRESSING TUBULAR ENDOPROSTHESES AND FOR INSERTING A COMPRESSED ENDOPROSTHESIS INTO AN APPLICATION TUBE

(75) Inventor: Peter Eisenkolb, Kempten (DE)

(73) Assignee: Karl Storz GmbH & Co. KG (DE)

( * ) Notice: Subject to any disclaimer, the term of this patent is extended or adjusted under 35 U.S.C. 154(b) by 604 days.

(21) Appl. No.: 10/863,570

(22) Filed: Jun. 8, 2004

(65) Prior Publication Data

US 2005/0021122 A1 Jan. 27, 2005

Related U.S. Application Data

(63) Continuation of application No. PCT/EP03/11281, filed on Oct. 11, 2003.

(30) Foreign Application Priority Data

Oct. 26, 2002 (DE) ................................ 102 49 927

(51) Int. Cl.
*A61M 29/00* (2006.01)
(52) U.S. Cl. ..................................................... 606/198
(58) Field of Classification Search ................ 623/1.11, 623/1.12, 1.15; 606/108, 191–198, 1
See application file for complete search history.

(56) References Cited

U.S. PATENT DOCUMENTS

| 5,630,830 | A | * | 5/1997 | Verbeek | 606/198 |
| 5,672,169 | A | * | 9/1997 | Verbeek | 623/1.15 |
| 5,676,671 | A | | 10/1997 | Inoue | 606/108 |
| 6,132,358 | A | * | 10/2000 | Glenn et al. | 600/3 |
| 2002/0040236 | A1 | | 4/2002 | Lau et al. | 623/1.12 |

FOREIGN PATENT DOCUMENTS

| DE | 100 04 979 A1 | 8/2000 |
| EP | 0 519 282 A1 | 12/1992 |
| GB | 2 234 138 | * 9/2000 |

* cited by examiner

*Primary Examiner*—Kevin T Truong
(74) *Attorney, Agent, or Firm*—St. Onge Steward Johnston & Reens LLC

(57) ABSTRACT

The invention relates to a device for compressing tubular endoprostheses and for inserting a compressed endoprosthesis into an application tube. A device that is simple to handle and can be used to the fullest possible extent without manual contact with the endoprosthesis is characterized, according to the invention, by a tubular prosthesis receptor consisting of at least two parts that can move with respect to one another and with its inner lumen in the closed state equal to the outer diameter of the compressed endoprosthesis, and by a folding tool that can be inserted into the prosthesis receptor with the endoprosthesis to form a lengthwise fold aimed inward in the endoprosthesis.

17 Claims, 3 Drawing Sheets

DEVICE FOR COMPRESSING TUBULAR ENDOPROSTHESES AND FOR INSERTING A COMPRESSED ENDOPROSTHESIS INTO AN APPLICATION TUBE

This application is a continuation of pending International Patent Application No. PCT/EP03/11281 filed Oct. 11, 2003, which designates the United States and claims priority of pending German Patent Application No. 102 49 927.6 filed Oct. 26, 2002.

FIELD OF THE INVENTION

The invention relates to a device for compressing tubular endoprostheses, especially stents, and for inserting a compressed endoprosthesis into an application tube.

In surgery, endoprostheses are defined as small endoscopically placed tubes, so-called stents or tubuses, for bypassing or draining in the event of stenosis, strictures, and tumors. Stents are self-expanding tubular prostheses that can be produced from various bodily compatible materials and which, after the endoscopic or radiological implantation, expand independently, for instance with tumor-conditioned stenosis and obstruction or with arteriosclerotically conditioned short-term vessel stenosis, to bypass or secure the lumen of a hollow organ.

The endoprostheses are usually implanted by means of an application tube, into which the prosthesis is inserted in a compressed or folded condition so that it can be pressed out of the application tube again in the operating area under endoscopic observation by means of a suitable expressing tool. In the operating area the endoprosthesis is again unfolded so that it can be secured onto the expected place on the hollow organ. Patent DE 100 04 979 A describes a system for inserting endoprostheses which, in addition to the device for compressing tubular endoprostheses and for inserting a compressed endoprosthesis into an application tube, also includes the complete endoscopic operating set in order to insert the prosthesis into the operating area by way of the application tube. In this system the endoprosthesis is compressed and inserted into the application tube by means of a compressing and inserting device, which consists of two tubular segments that can be slid into one another and which in turn can be secured onto the application tube.

In order to insert the endoprosthesis into the application tube completely compressed, that is folded to form a longitudinal roll shape, the prosthesis is first pressed manually in lengthwise direction in such a way that a longitudinal fold is formed extending inward into the hollow interior of the prosthesis. This endoprosthesis, manually compressed in such a manner, is now inserted manually into the outer tubular part of the compression and insertion device. Then the free end of this tubular part is closed with a plug and the tubular part equipped with the prosthesis is pushed in the direction of the inner of the two tubular parts of the compression and insertion device which is secured on the application tube. By thus pushing the tubular parts against one another, the endoprosthesis is pressed inside the application tube and is thereby further compressed.

In addition to the fact that the compression and insertion device consisting of the two tubular parts is expensive and complex in terms of construction and handling, this system has the further disadvantage that the endoprosthesis must first be manually folded and inserted into the compression and insertion device. Because endoprostheses as a rule are moistened with a slide gel, the prostheses are difficult to handle manually. In addition, slide gel gets dispersed and the operator's hands are wetted by the gel, hampering further work.

Consequently it is the object of the invention to provide a device of the aforementioned type for compressing tubular endoprostheses and for inserting a compressed endoprosthesis into an application tube, a device which is simple to operate and can be used to the greatest extent without manual contact with the endoprosthesis.

The invention fulfills this object in a manner characterized by a tubular prosthesis receptor consisting of at least two parts that can move with respect to one another and whose inner lumen in the closed state is essentially equal to the outer diameter of the compressed endoprosthesis, and is also characterized by a folding tool that can be inserted with the endoprosthesis in the prosthesis receptor and serves to form a lengthwise fold in the endoprosthesis directed toward the inside.

Owing to the inventive design of the device consisting of the prosthesis receptor and the folding tool, it is possible for the first time to compress an endoprosthesis almost entirely without manual contact and to insert it in an application tube. In addition the simple structure of the inventive device allows a simple, rapid, and safe operation without risk of damage to the endoprosthesis.

According to a preferred embodiment of the invention, the prosthesis receptor consists of two half-tubular parts that can rotate with respect to one another on a hinge and into which the endoprosthesis is inserted. Then, by means of the hinge, which can be configured for instance as a film hinge, the prosthesis receptor can be locked in simple manner to compress the endoprosthesis, after the lengthwise fold, directed inward, has been configured in the endoprosthesis by means of the folding tool.

The parts of the prosthesis receptor that are movable with respect to one another can be fixed to one another by means of a locking mechanism such as a slide bolt when the prosthesis receptor is closed The folding tool can advantageously be configured as an essentially cylindrical rod, since such a cylindrical rod can be produced simply and economically and, thanks to its geometric design, without the risk of damage to the endoprosthesis during formation of the fold To facilitate insertion of the compressed endoprosthesis into the application tube, the invention proposes that a section be made in the prosthesis receptor on the distal side to expand the inner lumen for reception of the application tube, so that the inner diameter of the enlarged section is essentially equal to the outer diameter of the application tube. By configuring this section with expanded inner diameter, a guidance groove for the application tube has been formed in the prosthesis receptor.

The transition from the section with the expanded inner diameter to the smaller lumen of the prosthesis receptor thus forms an essentially circular buffer surface for the application tube that is to be inserted, and the radial height of the buffer surface is equal at least to the wall thickness of the application tube in order to avoid damage to the endoprosthesis on insertion into the application tube.

In a practical embodiment of the invention it is further proposed that the device should include a ground plate to receive the prosthesis receptor and the folding tool. This ground plate consists preferably of a rectilinear base plate and two studs arranged on facing sides of the base plate, with the distance between the studs equal to at least the maximum length of the prosthesis receptor.

To ensure secure and exact storage of the prosthesis receptor on the base plate of the ground plate, a guide groove is configured in the base plate to receive a corresponding guide ridge of the prosthesis receptor. This guide ridge of the prosthesis receptor can be formed, for instance, by the hinge connecting the individual parts of the prosthesis receptor to one another.

The folding tool is secured to the ground plate, according to the invention, by recesses in the studs which contain and receive the folding tool. It is proposed, in practical embodiments, that the distal-side end of the folding tool should be spherical in shape to ensure tippable storage in one of the studs, and in the area of the proximal end of the folding tool, on the folding tool, there should be a bolting element by means of which the folding tool can be secured in the corresponding recess of the other stud.

To facilitate use of the folding tool, it is further proposed that a handle should be mounted on the proximal end of the folding tool.

The compressed endoprosthesis mounted in the closed prosthesis receptor of the invention device is inserted by means of an expressing tool, with which the compressed endoprosthesis is pushed out of the prosthesis receptor into the application tube.

It is finally proposed with the invention that the endoprosthesis compressed by means of the inventive device should be insertable into a hollow organ endoscopically or radiologically by means of the application tube.

Additional characteristics and advantages of the invention are presented in the following description of the associated illustrations, depicting in schematic, exemplary fashion an embodiment of an inventive device for compressing tubular endoprostheses and for inserting a compressed endoprosthesis into an application tube.

DETAILED DESCRIPTION OF THE DRAWINGS

Figure 1:
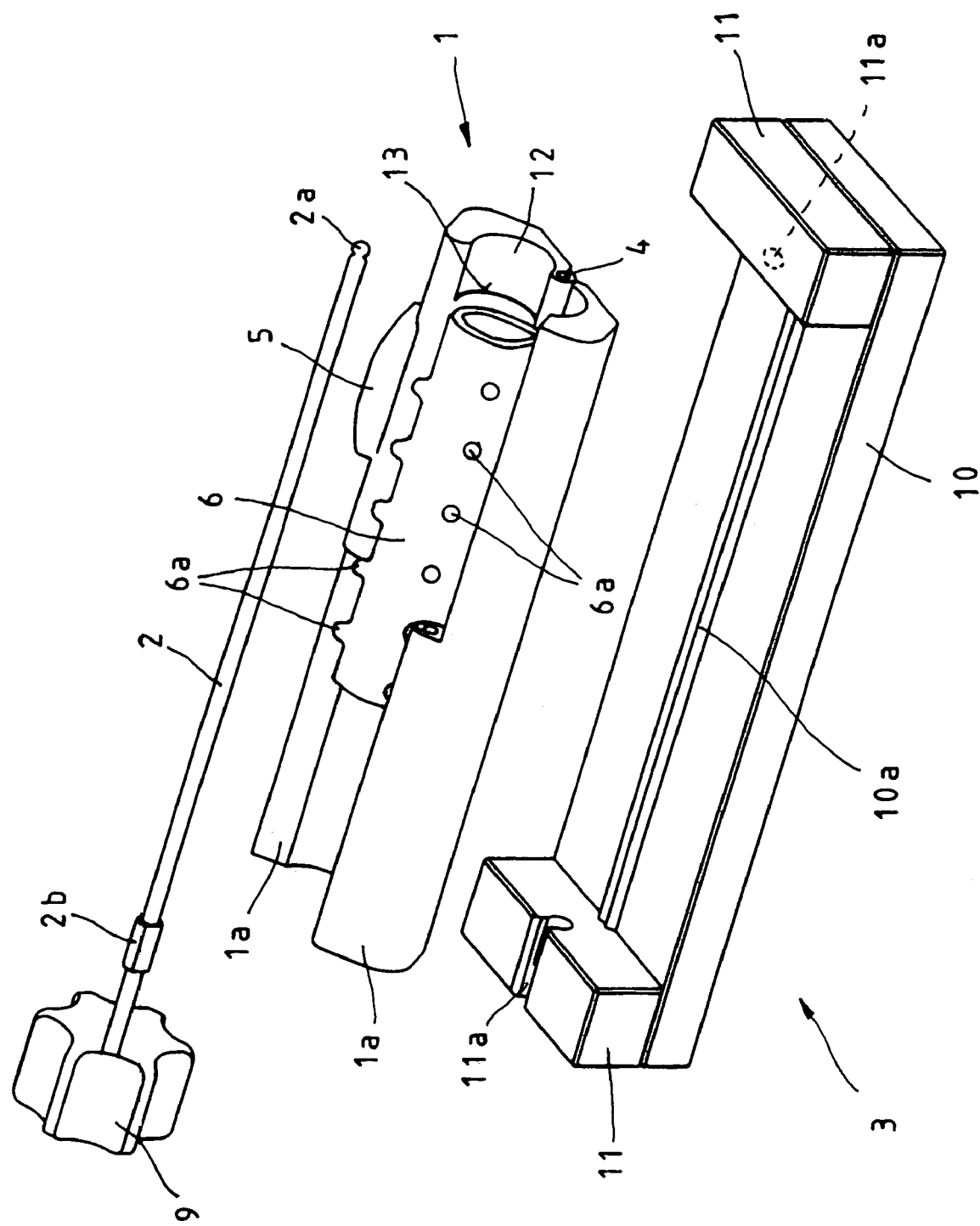
FIG. 1 shows a perspective explosion view of an inventive device in open position with inserted endoprosthesis.
Figure 2:
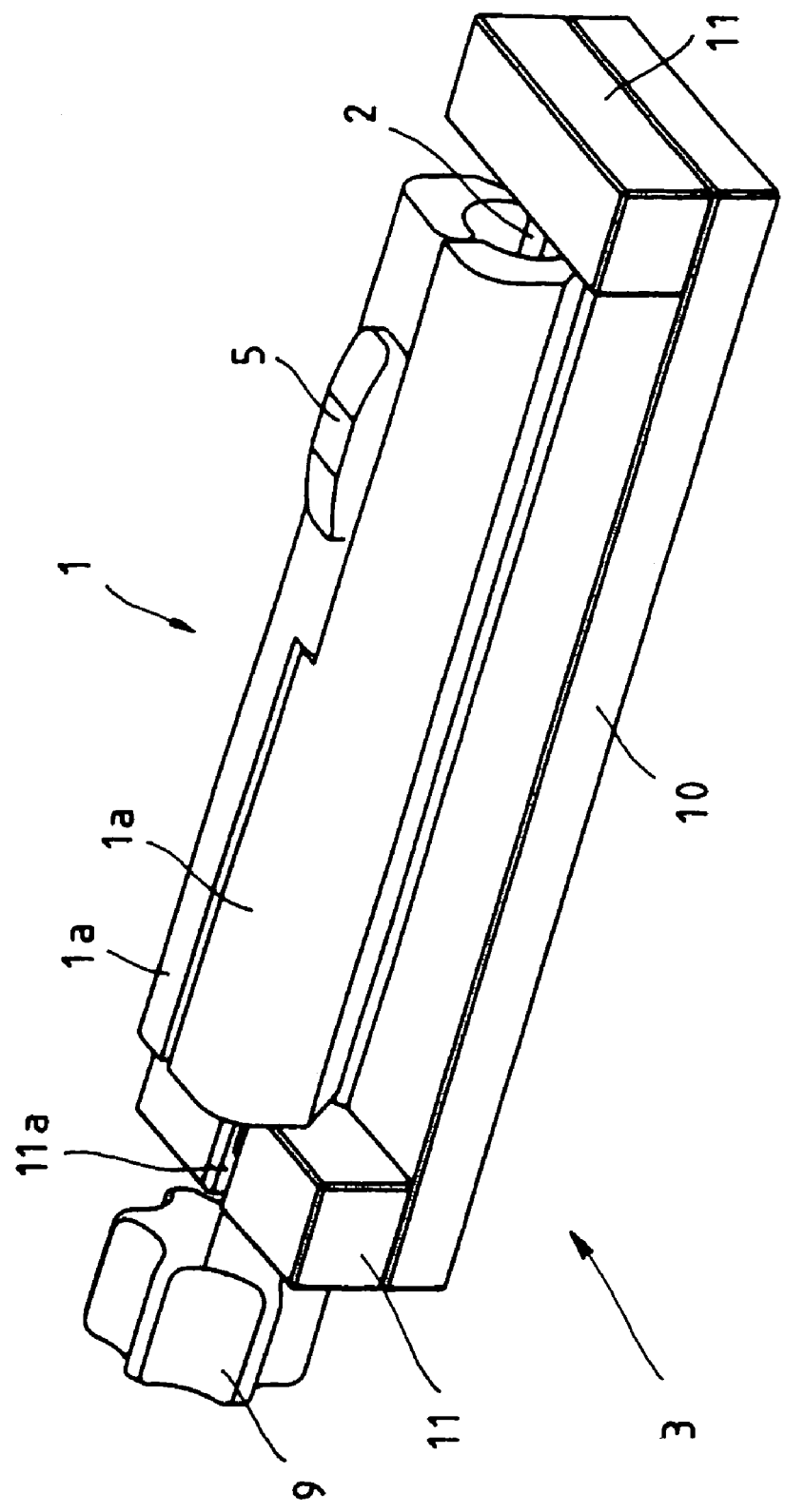
FIG. 2 shows a perspective view of the device in FIG. 1 but showing the device together and in closed position.

The device, illustrated in FIGS. 1 and 2, for compressing tubular endoprostheses and for inserting a compressed endoprosthesis into an application tube consists essentially of a prosthesis receptor 1, a folding tool 2, and a ground plate 3 to receive and store both the prosthesis receptor 1 and the folding tool 2.

As can further be seen from the illustrations, the prosthesis receptor 1 consists in the illustrated embodiment of two half-tubular parts 1a, which are jointed together by means of the hinge 4 in such a way that the prosthesis receptor 1 can be moved by means of the hinge 4 between an open position (FIG. 1) and a closed position (FIG. 2). To secure the prosthesis receptor 1 in the closed position, the prosthesis receptor has a bolting mechanism 5 by means of which the two parts 1a can be secured to one another.

In the illustrated embodiment, the bolding mechanism 5 is shown as a slide bolt. Other forms of bolding mechanism 5 can of course be used, such as a notch and clamp lever. Likewise, the structure of the prosthesis receptor 1 is not restricted to having two parts 1a that can rotate with respect to one another; instead it is also possible to configure the prosthesis receptor 1 from three or more parts 1a, which can be joined together to form a closed tubular prosthesis receptor 1 by means of rotation, joining, inserting, or pushing together.

Figure 4:
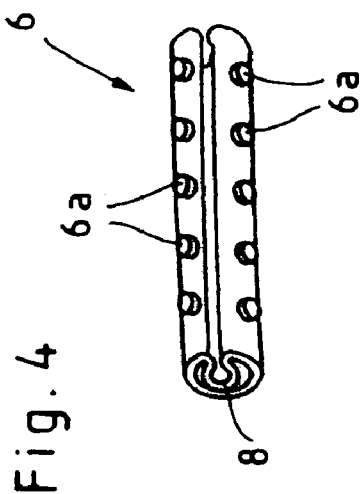
FIG. 4 shows a perspective view of the compressed endoprosthesis.

As shown in FIG. 1, the prosthesis receptor serves to receive a tubular endoprosthesis 6, which can be converted into the illustrated compressed state shown in FIG. 4 by means of the prosthesis receptor 1 and the folding tool 2. In this compressed state, the endoprosthesis 6 can be inserted into an application tube 7 and then endoscopically or radiologically inserted into a hollow organ, for instance into the air tubes, bronchial tubes, or blood vessels, where the endoprosthesis 6 unfolds itself again independently and takes the shape shown in FIG. 1.

The endoprosthesis 6 shown in FIG. 1 is a simple tubular endoprosthesis 6 on whose outside surface several knobs 6a are placed at intervals on the radius and serve to ensure that the endoprosthesis 6 is supported against the inside wall of the particular hollow organ and that the endoprosthesis 6 is anchored in a precise location. Besides the illustrated shape of a simple tubular endoprosthesis 6, it is also possible of course for different forms of endoprostheses 6 such as, for instance, Y prostheses, to be compressed with this device and inserted into an application tube 7.

Because the lumen of the closed prosthesis receptor 1 is clearly smaller than the outer diameter of the unfolded endoprosthesis 6, upon compression of the endoprosthesis 6 a lengthwise fold 8 is made in the endoprosthesis 6 in the prosthesis receptor 1 by means of the folding tool 2, as can be seen in FIG. 4. When this lengthwise fold 8 is made, the outer diameter of the endoprosthesis 6 is clearly reduced and the sides of the folded endoprosthesis 6 can be pressed together upon the closing of the prosthesis receptor 1, thus further reducing the diameter of the endoprosthesis 6.

As can be seen from FIG. 1, the folding tool 2 to make the lengthwise fold 8 in the endoprosthesis 6 in the illustrated embodiment has a cylindrical rod shape, with a handle 9 on its proximal end.

The ground plate 3, which serves to receive and store the prosthesis receptor 1 as well as the folding tool 2, consists of a rectilinear base plate 10 as well as two studs 11 mounted on opposite sides of the base plate 10, with the distance between the two sides 11 equal to at least the axial length of the prosthesis receptor 1. To ensure exact positioning of the prosthesis receptor 1 on the base plate 10, the base plate 10 has a guide groove 10a into which the correspondingly shaped guide ridge of the prosthesis receptor 1 can be inserted. In the illustrated embodiment this guide ridge is made up of the hinge 4, by means of which the parts 1a of the prosthesis receptor 1 are joined together so they can rotate.

For storage of the folding tool 2, which in the present case has a cylindrical rod shape, recesses 11a are formed in the studs 11, into which the folding tool 2 can be secured, first by means of the spherical-shaped distal end 2a and second by means of a bolting element 2b, which is formed on the folding tool 2 in the area of the proximal end of the folding tool 2.

A device of this design for compressing tubular endoprostheses 6 and inserting a compressed endoprosthesis 6 into an application tube 7 operates as follows:

To allow implantation of an endoprosthesis 6 into a hollow organ by means of an application tube 7, it is necessary, first, to convert the endoprosthesis 6 from the completely folded form shown in FIG. 1 into the form shown in FIG. 4 in which the endoprosthesis 6 can be inserted for later implantation in an application tube 7.

In the first working step the completely unfolded endoprosthesis 6, as shown in FIG. 1, in the open position of the prosthesis receptor is inserted into the prosthesis receptor 1 mounted on the base plate 10 of the ground plate 3.

Then the folding tool 2 with its spherical distal end 2a is inserted in the recess 11a of the right-hand stud 11 of FIGS. 1 and 2 and the folding tool 2 is moved down until the bolting element 2b situated in the area of the proximal end of the folding tool 2 on the folding tool 2 is received in the recess 11a of the left-hand stud 1 in FIGS. 1 and 2. In this downward motion the folding tool 2 presses upon the endoprosthesis 6 mounted in the prosthesis receptor 1 in such a way that the lengthwise fold 8 shown in FIG. 4 is made in the endoprosthesis 6.

The bolting element 2b in the area of the proximal end of the folding tool 2 serves to secure the folding tool 2 in the downward-pressed position on the ground plate 3 so that the folding tool 2 is not raised up again by the material elasticity of the folded endoprosthesis 6.

In the next working step the half-tubular parts 1a of the prosthesis receptor 1 are rotated toward one another by the hinge 4 until the prosthesis receptor 1 assumes the closed position illustrated in FIG. 2. In this position the parts 1a of the prosthesis receptor 1 can be secured to one another by means of the bolting mechanism 5 so that the prosthesis receptor 1 can again be received by the ground plate 3 as is shown in FIG. 3.

In this position separated from the ground plate 3, it is now possible to pull the folding tool 2 out of the prosthesis receptor 1 again by means of the handle 9 by way of the proximal side of the prosthesis receptor 1, so that only the compressed endoprosthesis 6 is now found in the receptor 1.

Figure 3:
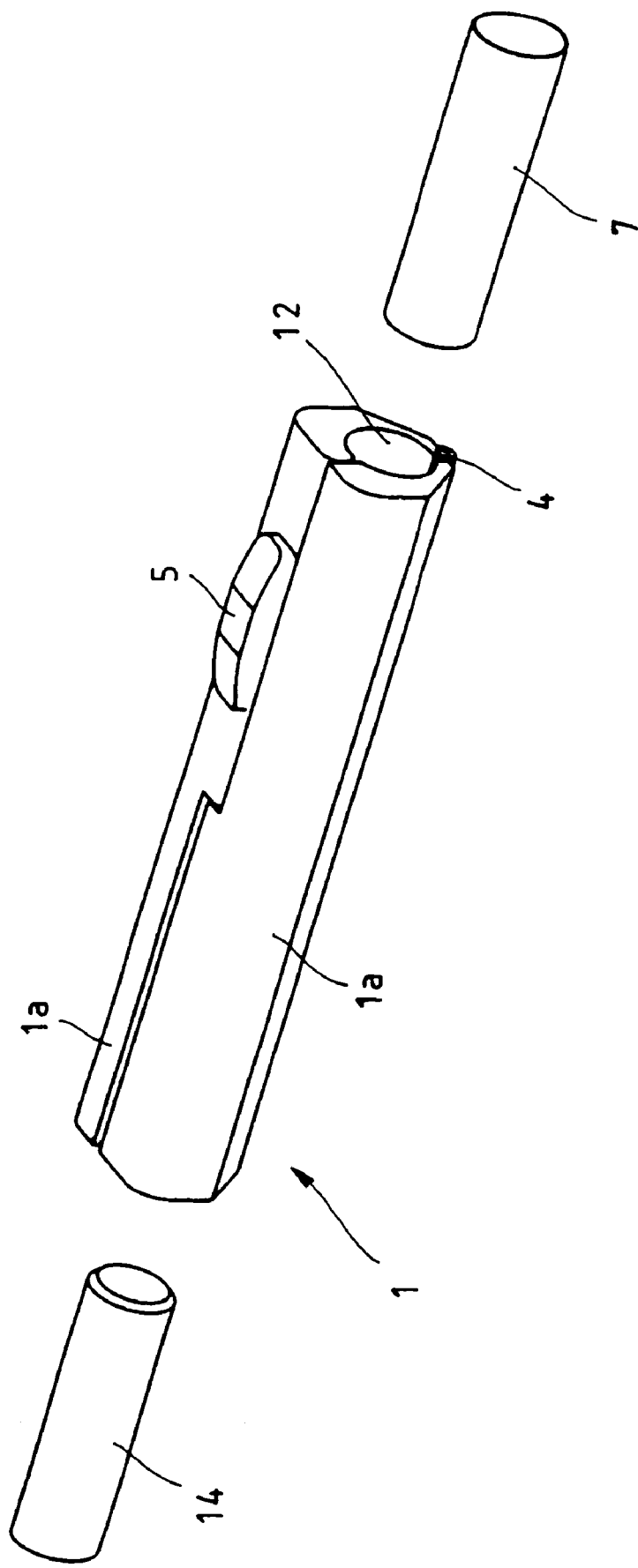
FIG. 3 shows a perspective view of the prosthesis receptor before the compressed endoprosthesis is pushed out.

To enable the compressed endoprosthesis 6 to be moved into the application tube 7, the application tube 7, as shown in FIG. 3, is pushed into the distal end of the prosthesis receptor 1. To ensure secure mounting and reception of the application tube 7, a section 12 is made in the prosthesis receptor 1 on the distal side to enlarge the inner lumen of the prosthesis receptor 1, with the inner diameter of the enlarged section 12 essentially equal to the outer diameter of the application tube 7.

The application tube 7 is thereby pushed far enough into the prosthesis receptor so that the application tube 7 is positioned against the essentially circular buffer surface 13 formed by the transition from the section 12 with the enlarged inner diameter to the smaller lumen of the prosthesis receptor 1.

The actual transport of the compressed endoprosthesis 6 into the application tube 7 occurs by means of a cylindrical expression tool 14, which is inserted into the prosthesis receptor 1 by the proximal end. By exerting additional pressure on the expression tool 14, the compressed endoprosthesis 6 is pushed out of the prosthesis receptor 1 into the application tube 7.

To prevent damage to the endoprosthesis 6 in pushing into the application tube 7, the radial height of the buffer surface 13 is at least equal to the wall thickness of the application tube 7, so that, in the transition from the inner lumen of the prosthesis receptor 1 into the application tube 7, only a harmless diameter increase can result, but in no case a shift to a narrower caliber that is dangerous for the endoprosthesis 6.

The compressed endoprosthesis 6, which is now in the application tube 7, can next be inserted endoscopically or radiologically into a hollow organ.

A device of this design for compressing tubular endoprostheses 6, and for inserting a compressed endoprosthesis 6 into an application tube 7, is distinguished in that the device can be operated to almost entirely without manual contact with the endoprosthesis 6 and can be handled in simple, safe, and rapid manner thanks to its simple construction.

Illustration Key
1 Prosthesis receptor
1a Part
2 Folding tool
2a Distal ends
2b Bolting element
3 Ground plate
4 Hinge
5 Bolting mechanism
6 Endoprosthesis
6a Knobs
7 Application tube
8 Lengthwise fold
9 Handle
10 Base plate
10a Guide groove
11 Stud
11a Recess
12 Expanded section
13 Buffer area
14 Expression tool

What is claimed is:

1. A device for compressing tubular endoprostheses and inserting a compressed endoprosthesis in an application tube distinguished by a tubular prosthesis receptor comprising two parts that move with respect to one another and whose interior lumen in a closed state is essentially equal to the outer diameter of the compressed endoprosthesis, and with a folding tool that is inserted with the endoprosthesis into the prosthesis receptor and forms a lengthwise fold aimed inward in the endoprosthesis; wherein a first part forms a first portion of the interior lumen in the closed state and a second part forms a second portion of the interior lumen in the closed state such that when the first and the second parts are brought together the interior lumen is formed.

2. A device as in claim 1, wherein the prosthesis receptor comprises two semi-tubular parts that can rotate with respect to one another by means of a hinge.

3. A device as in claim 2, wherein the hinge is configured as a film hinge.

4. A device as in claim 1, wherein the parts of the prosthesis receptor that can move with respect to one another can be secured to one another by means of a bolting mechanism in the closed position of the prosthesis receptor.

5. A device as in claim 1, wherein the folding tool is configured as an essentially cylindrical rod.

6. A device as in claim 1, wherein in the prosthesis receptor on the distal side a section that enlarges the inner lumen is made for receiving the application tube, with the inner diameter of the enlarged section essentially equal to the outer diameter of the application tube.

7. A device as in claim 6, wherein the transition from the section with the enlarged inner diameter to the smaller lumen of the prosthesis receptor forms an essentially circular buffer surface for the insertable application tube, with the radial height of the buffer surface equal to at least the wall thickness of the application tube.

8. A device as in claim 1, wherein there is a ground plate to receive the prosthesis receptor and the folding tool.

9. A device as in claim 8, wherein the ground plate comprises a rectilinear base plate and two studs mounted on opposite sides of the base plate, with the distance between studs equal to at least the axial length of the prosthesis receptor.

10. A device as in claim 9, wherein a guide groove is configured in the base plate to receive a corresponding guide ridge of the prosthesis receptor.

11. A device as in claim 10, wherein the hinge of the prosthesis receptor forms the guide ridge.

12. A device as in claim 11, wherein recesses are formed in the studs to store and receive the folding tool.

13. A device as in claim 12, wherein the distal end of the folding tube is spherical in shape for tippable storage in one of the studs.

14. A device as in claim 13, wherein in the area of the proximal end of the folding tool a bolting element is formed on the folding tool and can secure the folding tool in the correspondingly configured recess in one of the studs.

15. A device as in claim 14, wherein a handle is mounted on the proximal end of the folding tool.

16. A device as in claim 15, wherein the compressed endoprosthesis mounted in the closed prosthesis receptor can be slid out of the prosthesis receptor into the application tube by means of an expression tool.

17. A device as in claim 16, wherein the compressed endoprosthesis can be inserted endoscopically or radiologically into a hollow organ by means of the application tube.

* * * * *